United States Patent
Korhonen et al.

(10) Patent No.: US 10,628,556 B2
(45) Date of Patent: Apr. 21, 2020

(54) METHOD AND APPARATUS FOR PROVIDING COLLABORATIVE PATIENT INFORMATION

(71) Applicant: CoreFOX Oy, Salo (FI)

(72) Inventors: Kimmo Sakari Korhonen, Salo (FI); Mika Juhani Hakala, Isokyrö (FI); Alex Erkko Johannes Kivikoski, Turku (FI); Tero Olavi Kuusinen, Kuusisto (FI); Jarmo Auvo Antero Lähteenmäki, Helsinki (FI); Johanna Marketta Nordblad, Helsinki (FI); Mika Jukka Saari, Espoo (FI)

(73) Assignee: CoreFOX Oy, Salo (FI)

( * ) Notice: Subject to any disclaimer, the term of this patent is extended or adjusted under 35 U.S.C. 154(b) by 1016 days.

(21) Appl. No.: 15/064,838

(22) Filed: Mar. 9, 2016

(65) Prior Publication Data
US 2016/0314277 A1    Oct. 27, 2016

(30) Foreign Application Priority Data

Mar. 10, 2015    (FI) ..................... 20155156

(51) Int. Cl.
*A61B 5/00*    (2006.01)
*G06Q 10/00*    (2012.01)
(Continued)

(52) U.S. Cl.
CPC .......... *G06F 19/3481* (2013.01); *G06F 19/00* (2013.01); *G16H 50/70* (2018.01)

(58) Field of Classification Search
CPC ........ G16H 50/20; G16H 10/60; G16H 50/70; G16H 40/63; G16H 50/50; G16H 50/30;
(Continued)

(56) References Cited

U.S. PATENT DOCUMENTS

| 6,971,972 B1 | 12/2005 | McGovern et al. |
| 2007/0179349 A1 | 8/2007 | Hoyme et al. |

(Continued)

FOREIGN PATENT DOCUMENTS

| WO | 2008134313 A1 | 11/2008 |
| WO | 2014/186780 A1 | 11/2014 |

OTHER PUBLICATIONS

Finnish Patent and Registration Office, Office Action, Application No. 20155156, dated Nov. 6, 2015, 6 pages.
(Continued)

*Primary Examiner* — Maroun P Kanaan
(74) *Attorney, Agent, or Firm* — Ziegler IP Law Group, LLC (57) ABSTRACT

A method for providing collaborative patient information, the method comprising receiving patient trauma information; generating patient rehabilitation information based on the patient trauma information; associating the patient trauma information and the patient rehabilitation information with a patient identifier to provide a collaborative patient record; automatically providing a set of exercises from a database based on the collaborative patient record; receiving selection for at least one physical exercise from the set of physical exercises and providing audio-visual training information relating to the selected physical exercises to be added to the patient rehabilitation information; providing the audio-visual training information to be available for the patient; receiving feedback information relating to the training information and adding the feedback information to the collaborative patient record; and determining an automatic alert using at least one of the following: the patient trauma information; the patient rehabilitation information; and the feedback information.

20 Claims, 4 Drawing Sheets

(51) Int. Cl.
*G06F 19/00* (2018.01)
*G16H 50/70* (2018.01)

(58) Field of Classification Search
CPC ........ G16H 50/80; G16H 30/20; G16H 30/40; G16H 20/13; G06F 19/3418; G06T 2210/41; G06T 2207/20081; G02B 2027/0138; G02B 2027/014
See application file for complete search history.

(56) References Cited

U.S. PATENT DOCUMENTS

| | | |
|---|---|---|
| 2008/0281633 A1 | 11/2008 | Burdea et al. |
| 2010/0191071 A1 | 7/2010 | Anderson et al. |
| 2013/0006659 A1 | 1/2013 | Mills |
| 2014/0081658 A1 | 3/2014 | Irving et al. |
| 2014/0081659 A1 | 3/2014 | Nawana et al. |
| 2014/0081661 A1* | 3/2014 | Fu ................. G06F 19/3481 705/3 |
| 2014/0172460 A1 | 6/2014 | Kohli et al. |
| 2014/0257854 A1* | 9/2014 | Becker ............... G06F 19/321 705/3 |
| 2015/0088547 A1* | 3/2015 | Balram ............. G06F 19/3418 705/3 |
| 2015/0213225 A1* | 7/2015 | Amarasingham ....... G06F 19/00 705/2 |

OTHER PUBLICATIONS

Extended European Search Report received for European Patent Application No. EP16159348.8, dated Aug. 2, 2016, 8 pages.
Second Search Report received for Finnish Patent Application No. FI20155156, dated May 19, 2016, 2 pages.

* cited by examiner

METHOD AND APPARATUS FOR PROVIDING COLLABORATIVE PATIENT INFORMATION

TECHNICAL FIELD

The present application generally relates to providing collaborative patient information, especially relating to a trauma of a patient, rehabilitation relating to the trauma and feedback during the rehabilitation.

BACKGROUND

This section illustrates useful background information without admission of any technique described herein representative of the state of the art. Many traumas require rehabilitation and special physical exercises with intensive follow-up. Before rehabilitation a diagnosis by a doctor is typically required. However, the distance between the patient, the doctor and the therapist may be remarkable that makes the overall process and information flow between the parties difficult. Furthermore, the existing systems lack a dynamic service system that would enable controlling and follow-up of the overall process for the patient data relating to the trauma and its rehabilitation. That makes the current systems ineffective, slow and difficult to control.

Thus, a service solution is needed to enable analysis, physical/mental training and on-line follow up with a build-in state of the art rehabilitation process. For the patient the system should provide overall rehabilitation instructions from the first appointment with a physician/doctor/psychologist to the patient's smartphone, tablet, computer or similar device.

SUMMARY

Various aspects of examples of the invention are set out in the claims.

According to a first example aspect of the present invention, there is provided a method, at a service server, for providing collaborative patient information, the method comprising:
  receiving multimedia data, from a user apparatus, relating to a patient trauma captured by a second user;
  maintaining history data of a plurality of reference collaborative patient records of other patients comprising information on multimedia data for different patient traumas;
  comparing the received multimedia data with the history data;
  selecting, based on the comparison, at least one reference collaborative patient record;
  determining, based on the selected reference collaborative patient record, patient trauma information;
  generating patient rehabilitation information based on the patient trauma information;
  associating the patient trauma information and the patient rehabilitation information with a patient identifier to provide a collaborative patient record accessible by a first user, the second user and a third user;
  automatically providing a set of exercises from a database based on the collaborative patient record;
  receiving selection, from the third user, for at least one exercise from the set of exercises and providing audio-visual training information relating to the selected exercises to be added to the patient rehabilitation information;
  providing the audio-visual training information to be available for the patient;
  receiving feedback information relating to the training information and adding the feedback information to the collaborative patient record; and
  determining an automatic alert using at least one of the following: the patient trauma information; the patient rehabilitation information; and the feedback information.

In an embodiment, the exercise comprises at least one of a physical exercise and/or a mental exercise.

In an embodiment, the patient rehabilitation information comprises a dynamic rehabilitation diary defining the exercise to be performed in a timely manner and maintaining status of the performance of the exercise, and the method further comprising: determining the automatic alert based on the dynamic rehabilitation diary; and sending the automatic alert to a user apparatus of the patient.

In an embodiment, the method further comprises sending the automatic alert to a user apparatus of a care person. The care person may be a dedicated person having access to at least part of the collaborative patient record.

In an embodiment, the method further comprises sending the automatic alert to a user apparatus of a doctor providing the patient trauma information.

In an embodiment, the method further comprises sending the automatic alert to a user apparatus of a physiotherapist providing the selection for at least one physical exercise of the patient rehabilitation information.

In an embodiment, the method further comprises: receiving an update for the dynamic rehabilitation diary defining the at least one physical exercise; and updating the dynamic rehabilitation diary defining the at least one physical exercise to be performed in a timely manner.

In an embodiment, the dynamic rehabilitation diary defines a plurality of physical exercises each to be performed in a timely manner.

In an embodiment, the method further comprises: receiving a new physical exercise with audio-visual training information; and adding the new physical exercise with the audio-visual training information to the database.

In an embodiment, the method further comprises requesting feedback information after each physical exercise being performed based on changed performance status of the physical exercise in the dynamic rehabilitation diary.

In an embodiment, the requested feedback comprises a pain scale questionnaire.

In an embodiment, the method further comprises: receiving answers to the pain scale questionnaire and converting the answers to the feedback information relating to the training information and adding the feedback information to the collaborative patient record; and generating a report based on the feedback information.

In an embodiment, the method further comprises sending the automatic alert to a user apparatus of a care person. The care person may be a dedicated person having access to at least part of the collaborative patient record.

In an embodiment, the method further comprises sending the report to a user apparatus of a doctor providing the patient trauma information.

In an embodiment, the method further comprises sending the report to a user apparatus of a physiotherapist providing the selection for at least one physical exercise of the patient rehabilitation information.

In an embodiment, the automatic alert to the user apparatus of the patient comprises instructions to perform a physical exercise defined by the dynamic rehabilitation diary.

According to a second example aspect of the present invention, there is provided a server apparatus comprising:
a communication interface for transceiving information over a network;
at least one memory including computer program code;
the at least one memory and the computer program code configured to, with the at least one processor, cause the server apparatus to:
receive multimedia data, from a user apparatus, relating to a patient trauma captured by a second user;
maintain history data of a plurality of reference collaborative patient records of other patients comprising information on multimedia data for different patient traumas;
compare the received multimedia data with the history data;
select, based on the comparison, at least one reference collaborative patient record;
determine, based on the selected reference collaborative patient record, patient trauma information;
generate patient rehabilitation information based on the patient trauma information;
associate the patient trauma information and the patient rehabilitation information with a patient identifier to provide a collaborative patient record accessible by a first user, the second user and a third user;
automatically provide a set of physical exercises from a database based on the collaborative patient record;
receive selection, from the third user, for at least one physical exercise from the set of physical exercises and providing audio-visual training information relating to the selected physical exercises to be added to the patient rehabilitation information;
provide the audio-visual training information to be available for the patient;
receive feedback information relating to the training information and adding the feedback information to the collaborative patient record; and
determine an automatic alert using at least one of the following: the patient trauma information; the patient rehabilitation information; and the feedback information.

In an embodiment, the at least one memory and the computer program code is further configured to, with the at least one processor, cause the server apparatus to:
maintain history data of a plurality of reference collaborative patient records of other patients comprising information on rehabilitation times for different patient traumas;
compare the received patient trauma information with the history data;
select, based on the comparison, at least one reference collaborative patient record; and
determine an estimated rehabilitation time for the patient based on the selected reference collaborative patient record and the collaborative patient record.

In an embodiment, the at least one memory and the computer program code is further configured to, with the at least one processor, cause the server apparatus to:
maintain history data of a plurality of reference collaborative patient records of other patients comprising information on rehabilitation times for different patient traumas;
compare the received patient trauma information with the history data;
select, based on the comparison, at least one reference collaborative patient record;
determine, based on the selected reference collaborative patient record and the collaborative patient record, selection for at least one further physical exercise from the set of physical exercises and providing audio-visual training information relating to the selected physical exercises to be added to the patient rehabilitation information; and
provide the audio-visual training information to be available for the patient.

In an embodiment, the at least one memory and the computer program code is further configured to, with the at least one processor, cause the server apparatus to:
compare the received multimedia data with the history data;
select, based on the comparison, at least one reference collaborative patient record;
determine, based on the selected reference collaborative patient record, preliminary patient trauma information;
provide the preliminary patient trauma information for an approval; and
receiving the patient trauma information in response to the approval.

In an embodiment, the exercise comprises at least one of a physical exercise and a mental exercise, and the patient rehabilitation information comprises a dynamic rehabilitation diary defining the exercise to be performed in a timely manner and maintaining status of the performance of the exercise, and wherein the at least one memory and the computer program code further configured to, with the at least one processor, cause the server apparatus to:
determine the automatic alert based on the dynamic rehabilitation diary; and
send the automatic alert to a user apparatus of the patient, wherein the automatic alert to the user apparatus of the patient comprising instructions to perform a physical exercise defined by the dynamic rehabilitation diary. The automatic alert may be sent to at least one of the following: a user apparatus of a doctor providing the patient trauma information; and a user apparatus of a physiotherapist providing the selection for at least one physical exercise of the patient rehabilitation information.

In an embodiment, the server apparatus is further configured to: receive an update for the dynamic rehabilitation diary defining the at least one physical exercise; and update the dynamic rehabilitation diary defining the at least one physical exercise to be performed in a timely manner.

In an embodiment, the first user comprises a doctor, the second user comprises a patient, and the third user comprises a therapist, and the first, second and third user are configured to generate collaborative patient information maintained as a collaborative patient record within the server apparatus.

In an embodiment, the server apparatus is further configured to request feedback information after each physical exercise being performed based on changed performance status of the physical exercise in the dynamic rehabilitation diary, wherein the requested feedback comprises a pain scale questionnaire.

In an embodiment, the server apparatus is further configured to receive answers to the pain scale questionnaire, convert the answers to the feedback information relating to the training information, and add the feedback information to the collaborative patient record; generate a report based on the feedback information; and send the report to at least one of the following: a user apparatus of a care person; a user apparatus of a doctor providing the patient trauma information; and a user apparatus of a physiotherapist providing the selection for at least one physical exercise of the patient rehabilitation information.

According to a third example aspect of the present invention, there is provided a computer program comprising computer executable program code configured to control an apparatus, when the computer executable program code is executed, to:
  receive multimedia data, from a user apparatus, relating to a patient trauma captured by a second user;
  maintain history data of a plurality of reference collaborative patient records of other patients comprising information on multimedia data for different patient traumas;
  compare the received multimedia data with the history data;
  select, based on the comparison, at least one reference collaborative patient record;
  determine, based on the selected reference collaborative patient record, patient trauma information;
  generate patient rehabilitation information based on the patient trauma information;
  associate the patient trauma information and the patient rehabilitation information with a patient identifier to provide a collaborative patient record accessible by a first user, the second user and a third user;
  automatically provide a set of physical exercises from a database based on the collaborative patient record;
  receive selection, from the third user, for at least one physical exercise from the set of physical exercises and provide audio-visual training information relating to the selected physical exercises to be added to the patient rehabilitation information;
  provide the audio-visual training information to be available for the patient;
  receive feedback information relating to the training information and adding the feedback information to the collaborative patient record; and
  determine an automatic alert using at least one of the following: the patient trauma information; the patient rehabilitation information; and the feedback information.

According to a fourth example aspect of the present invention, there is provided a user apparatus comprising:
  a sensor for capturing user health data;
  a communication interface for transceiving information over a network;
  at least one memory including computer program code;
    the at least one memory and the computer program code configured to, with the at least one processor, cause the apparatus to:
    transmit user health data for patient trauma information determination;
    receive audio-visual training information, wherein patient rehabilitation information is generated, at the server apparatus, based on the determined patient trauma information, the patient trauma information and the patient rehabilitation information are associated with a patient identifier to provide a collaborative patient record, a set of exercises are automatically provided from a database based on the collaborative patient record, and a selection is automatically provided for at least one exercise from the set of exercises and audio-visual training information is further provided relating to the selected exercises to be added to the patient rehabilitation information;
    transmit feedback information relating to the training information for adding the feedback information to the collaborative patient record; and
    receive an automatic alert generated by the server apparatus using at least one of the following: the patient trauma information; the patient rehabilitation information; and the feedback information.

In an embodiment, the user apparatus comprises a client application of a collaboration patient data service whose server application is running on the server apparatus. The client application may be configured to capture the multimedia data and/or to retrieve metadata for the captured multimedia data from metadata elements of the user apparatus. The client application may be configured to access the collaborative patient record and receive rehabilitation recommendation to be followed by the user of the user apparatus.

Different non-binding example aspects and embodiments of the present invention have been illustrated in the foregoing. The embodiments in the foregoing are used merely to explain selected aspects or steps that may be utilized in implementations of the present invention. Some embodiments may be presented only with reference to certain example aspects of the invention. It should be appreciated that corresponding embodiments may apply to other example aspects as well.

BRIEF DESCRIPTION OF THE DRAWINGS

For a more complete understanding of example embodiments of the present invention, reference is now made to the following descriptions taken in connection with the accompanying drawings in which.

DETAILED DESCRIPTION OF THE DRAWINGS

An example embodiment of the present invention and its potential advantages are understood by referring to FIGS. 1 through 6 of the drawings. In this document, like reference signs denote like parts or steps.

Figure 1:
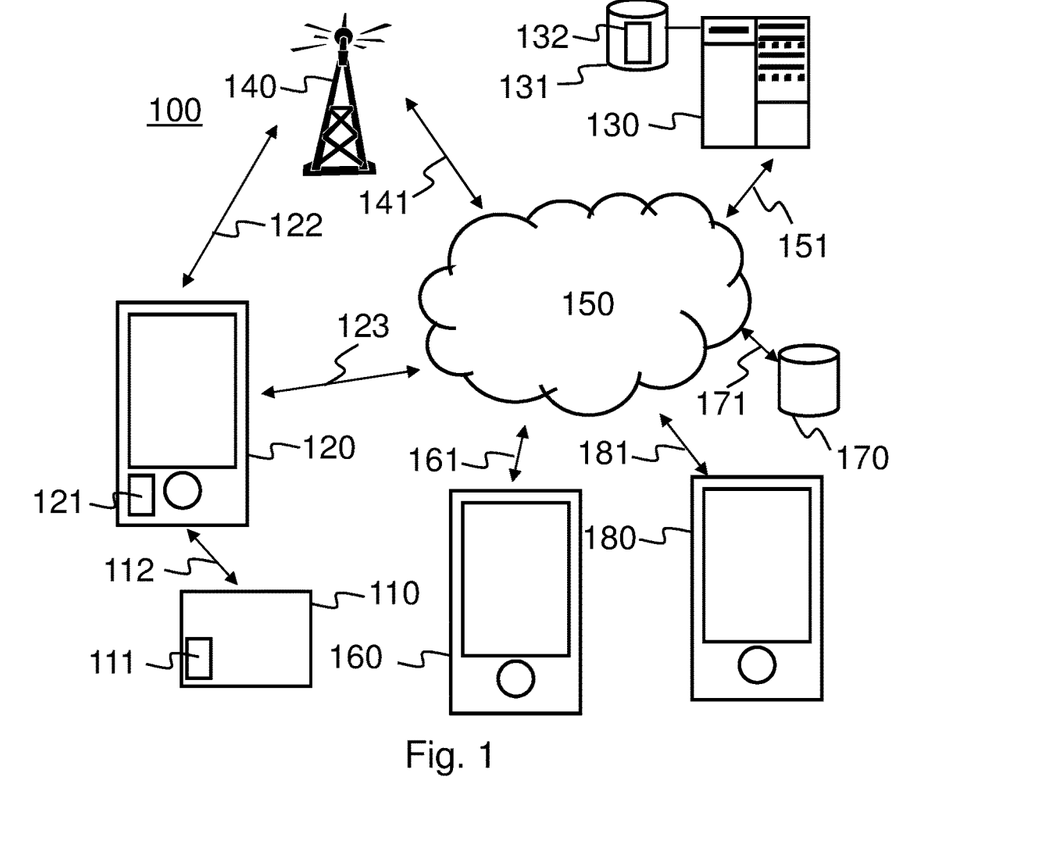
FIG. 1 shows a schematic drawing of a system of an example embodiment.

FIG. 1 shows a schematic picture of a system 100 according to an example embodiment of the invention. The system 100 comprises a user device 110 configured to be capable of capturing physical exercise related data. The user device 110 may comprise storage 111 for the physical exercise data. The storage 111 may comprise a flash memory card, for example. The user device 110 is configured to be connectable to a user apparatus 120 over a data connection 112. The data connection 112 may be a wired connection or a wireless connection. The wired connection may comprise Universal Serial Bus (USB), High-Definition Multimedia Interface (HDMI) or local area network (LAN), for example.

The wireless connection may comprise Bluetooth™, Radio Frequency Identification (RF-ID) or wireless local area network (WLAN), for example.

The user device 110 is configured to send captured data over the data connection 112 to the user apparatus 120. Such transmittal may be initiated by a user of the user device 110, by a user of the user apparatus 120, or automatically based on settings. Such settings may comprise for example time of the day, amount of newly captured exercise data or existence of the data connection 112 for the user device 110.

The user apparatus 120 may comprise a multimedia device 110, a mobile phone, an Internet tablet or a laptop computer, for example. The user apparatus 120 is capable of downloading and locally executing software program code. The software program code may be a client application of a service whose server application is running on the server apparatus 130 of the system 100. The user apparatus 120 may comprise physical exercise capturing element, such as an accelerometer or a camera, for capturing physical exercise data, such as movements, for example. The user apparatus 120 may also have a metadata element 121 for creating data usable as metadata of the physical exercise data captured by the user device 110. The metadata element 121 may comprise at least one of the following: a microphone, a positioning device for determining the current location of the user apparatus 120, and a clock. The user apparatus 120 is configured to be connectable to a wireless communication network 140 over a wireless connection 122. The wireless connection 122 may comprise a mobile cellular network or a wireless local area network (WLAN), for example. The wireless communication network 140 may be connected to a public data communication network 150, for example to the Internet, over a data connection 141. The client application may be operable also in offline mode and there is no need to have online connection over the network to the server 130, 131 all the time. In offline mode, the user apparatus 120 or user device 110 may store application related data to cache memory and update the data to the server 130, 131 once getting the online access.

In an embodiment, a second user, for example a patient, may capture multimedia data relating to his trauma using a second user apparatus 120 or a user device 110. Such multimedia data may comprise still images or video stream. The multimedia data may be sent from the user apparatus 120 to the system server 130. At the system server 130, the received multimedia data may be automatically analysed to prepare preliminary patient trauma information, for example. Automatic analysis may comprise, for example, pattern recognition and image recognition, wherein history data of other patients and their multimedia data may be used for comparison. Thus, early trauma information may be defined even before the patient visits the doctor. The patient may be a human or an animal. In case of the animal, an owner of the animal may operate the user apparatus 120 and provide necessary interaction with the system 100.

In an embodiment, the system 100 comprises a server apparatus 130, which comprises a storage device 131 for storing collaborative patient information, such as physical/mental exercise data and/or metadata received over a data connection 151, patient information of users, trauma information of patients, rehabilitation information, training data and diaries, for example. The trauma may comprise a physical or psychological trauma. The collaborative patient information may further comprise description of physician's/psychologist's diagnose, holistic rehabilitation process description, a large library of audio-visual exercises, a rehabilitation diary, and nutrition guidance to support the rehabilitation process.

In an embodiment, the system 100 may further comprise other user apparatuses 160, 180, connected to the network 150 over connections 161, 181 respectively, wherein tasks relating to the service system may be processed. The user apparatus 160 may comprise the user apparatus of a doctor producing the trauma information of a patient, for example. The user apparatus 180 may comprise the user apparatus of a therapist (physical or mental) defining the rehabilitation information of the patient, based on the trauma information, for example. The user apparatus 120 may comprise the user apparatus of the patient, for example.

In an embodiment, a first user apparatus 160 may be operated by a doctor as a first user. The first user may study, using the first user apparatus 160, service system data maintained in the server apparatus 130 relating to the patient. The data may be saved by the patient before coming to meet the doctor. The data may comprise, for example, information relating to exercises, medicine, sensation of the pain and performance and general comments. The patient data may have been transmitted to the server 130 from the user apparatus 120 and then again, after processing, from the server 130 over data connections 151, 161 and network 150 to the user apparatus 160.

After reviewing the patient data and meeting the patient, the doctor diagnoses patient's trauma and adds patient trauma information to the collaborative patient record maintained in the server 130.

In an embodiment, the doctor may also define or update patient's physiotherapeutic examination and treatment referrals that are automatically saved to the system server 130 for the patient record. Data is immediately visible to all relevant parties, such as therapist, care person, patient, or health care, for example.

Different apparatuses 110, 120, 130, 160, 170, 180 may provide collaborative patient information to be maintained in the service system 100. The collaborative patient information may be maintained as a collaborative patient record 132 within the server apparatus 130, 131. The collaborative patient record 132 may comprise any patient related information provided by different users, the service system or sensors, for example.

Furthermore, the doctor may define rehabilitation targets and recommendations, together with assessing the level of the trauma. The doctor may also add nutrition guides and accept the predefined rehabilitation recommendation for diagnosed trauma. The system service may receive trauma information defined by the doctor as input and provide automatically a predefined proposal for rehabilitation recommendation based on the trauma information. History data of all patients may be used for defining proposed rehabilitation recommendations. The doctor approved patient rehabilitation information is maintained in the collaborative patient record associating the patient trauma information and the patient rehabilitation information with the patient identifier to provide a collaborative patient record.

In an embodiment, a server apparatus 130 maintains, by an operator, the service system data, such as collaborative patient records. The patient records may comprise, for example, patient trauma information, the patient rehabilitation information, and feedback information. Each patient record may be identified using a patient identifier. The patient identifier may comprise, for example a social security number or a personal e-mail address, for example.

Information relating to the collaborative patient records may be transmitted to the server 130 from a plurality of apparatuses 120, 160, 180 over the network 150. Eventually, the received service data is maintained, by an operator, at the server 130 comprising storage device 131, wherein the data being available for users having access to that particular patient record. Furthermore, metadata associated with the service data may also be stored in the server 130 or storage device 131, such as location information, time information, or a device identifier, for example.

In an embodiment, a third user apparatus 180 may be operated by a therapist (physical or mental). The third user may have an access to the server apparatus 130 and the data available there. The third user may study, using the third user apparatus 180, service system data maintained in the server apparatus 130 relating to the patient. The data may be saved by the patient and the doctor before coming to meet the therapist. The data may comprise, for example, patient trauma information, patient rehabilitation information and information relating to exercises, medicine, sensation of the pain and performance and general comments. The patient data may have been transmitted to the server 130 from the user apparatuses 120, 160 and then again from the server 130 over data connections 151, 161 and network 150 to the user apparatus 180.

The third user, such as the physiotherapist, may also review from the patient record the earlier diagnoses, rehabilitations and recommendations.

After reviewing the patient data and meeting the patient, the physiotherapist examines patient's trauma and adds physical exercises to a dynamic rehabilitation diary defining the physical exercise to be performed in a timely manner and maintaining status of the performance of the physical exercise. The dynamic rehabilitation diary may be comprised by the collaborative patient record available at the server 130. The physical exercises added to the diary may comprise and provide audio-visual training information relating to the selected physical exercises.

In an embodiment, the physiotherapist may select a physical exercise from a library maintained in the system server 130. Alternatively, the physiotherapist may select a physical exercise from a local library maintained in the third apparatus 180.

In an embodiment, the physiotherapist may customize a totally new physical exercise on the fly. Patient information from the collaborative patient record may be used as input and the physiotherapist may utilize a camera application of the service system to generate audio-visual information for the exercise. After finalizing the audio-visual information, the physical exercise may be added to the dynamic rehabilitation diary. Camera and audio device of the third user apparatus 180 may be used for capturing the multimedia needed for the audio-visual information.

In an embodiment, the physiotherapist may also define or update the series and repetitions for all daily exercise sessions and storing this information to the dynamic rehabilitation diary as well.

Furthermore, all this data generated by the physiotherapist may be automatically saved to the system server 130 for the patient record. Data is immediately visible to all relevant parties, such as the patient and the doctor.

In an embodiment, a fourth user may be given access to the collaborative patient record in the server 130. Such four user may comprise, for example, a relative, a friend, a care person, a partner or an official linked with the patient, for example.

Any of the user apparatuses 120, 160, 180 may be operated as the first, second or third user apparatus. Same apparatus may also be used as the first, second and third user apparatus.

In an embodiment, patient related data generated by a patient may travel to a server apparatus 130 over different paths. A first path may comprise sending data captured by a proprietary application of a user apparatus 120 over a wireless communication network 122, 140, 141 and public data communication network 150, 151 to the server apparatus 130. A second path may comprise sending data captured by a default application of a user apparatus 120 over a wireless communication network 122, 140, 141 and public data communication network 150, 151 to the server apparatus 130. A third path may comprise sending data captured by an external device 110 (such as running mill or spinning device) to the user apparatus 120 over connection 112 and therefrom over a wireless communication network 122, 140, 141 and public data communication network 150, 151 to the server apparatus 130. A fourth path may comprise sending data captured by the device 110 to a computer apparatus 120 and therefrom over the connection 123 and the public data communication network 150, 151 to the server apparatus 130.

In an embodiment, the proprietary application in the user apparatus 120 may be a client application of a service whose server application is running on the server apparatus 130 of the system 100. The proprietary application may capture the data for the first path. Also metadata for the captured multimedia may be retrieved by the proprietary application from the metadata elements 121 of the user apparatus 120. The default application may be an exercising application of the user apparatus 120. For the second path, the multimedia data captured by the default application may be imported to the proprietary application before transmitting to the server apparatus 130. The proprietary application may check the data and extract and apply metadata for the multimedia data. For the third path, the data may be captured by the external device 110 and transmitted to the proprietary application of the user apparatus 120 for sending to the server apparatus 130. The proprietary application may check the data and extract and apply metadata for the multimedia data. User may provide additional metadata using the user apparatus 120. For the fourth path, the data may be captured by the external device 110 and transmitted to a communication application of a computer apparatus 120. The communication application may check the multimedia data and extract and apply metadata for the multimedia data. User may provide additional metadata using the computer apparatus. In a further embodiment, the user may access the data on the server apparatus and provide additional metadata.

In an embodiment, a proprietary or client application in the user apparatus 160 (e.g. doctor apparatus) defining the trauma information may be a client application of a service whose server application is running on the server apparatus 130 of the system 100. The proprietary application may also be utilized for setting rehabilitation information. Furthermore, the client application may be used to amend the stored data and settings later on.

In an embodiment, a proprietary or client application in the user apparatus 180 (e.g. therapist apparatus) defining and amending rehabilitation information may be a client application of a service whose server application is running on the server apparatus 130 of the system 100. Furthermore, the client application may be used to amend the data and settings later on.

In an embodiment, the external device 110 may comprise a user wearable device communicating with the apparatus 120 over a local connection 112. The local connection 112 may comprise, for example, at least one of the Bluetooth, Radio Frequency Identification (RF-ID), near field communication (NFC) or other wireless non-cellular connection. The wireless non-cellular connection may comprise industrial, scientific and medical (ISM) radio bands that are radio bands (portions of the radio spectrum) reserved internationally for the use of radio frequency (RF) energy for industrial, scientific and medical purposes, for example. Alternatively, the user wearable device 110 may be comprised by the apparatus 120, as illustrated by an integrated apparatus 121. The apparatus 110, 120, 121 may be for example a wrist wearable user apparatus.

In an embodiment, a communication interface module of the apparatus 120 may comprise location modules for tracking location of the portable apparatus 120. Such location modules may comprise a module for providing a connection to satellite based global positioning system (e.g. GPS, not shown), a module for cellular based positioning system, a module for wireless non-cellular positioning system (e.g. Wi-Fi) or a module for hybrid positioning system, for example. The positioning system may also be used for user speed detection, altitude detection, route detection and route planning for various embodiments.

In an embodiment, the apparatus 120 may be connected over a wireless or wired connection to a wide area network 150, such as Internet. Router apparatuses (not shown) may be used for providing the access to a wide area network 150. The access may comprise cellular or non-cellular connection.

In an embodiment, a proprietary application in the apparatus 120 may be a client application of a service whose server application is running on the server apparatus 130 of the system 100. The proprietary application may capture the user input data for the service and provide the user output data, for the service.

In an embodiment, history data of earlier physical exercises, characteristics of the physical exercises, user feedback information, trauma information and rehabilitation information may be maintained at the server 130. The server 130 may also provide a cloud service for the portable apparatus 120 data. Optionally, further apparatuses may be added, such as peripheral devices for maintaining, providing or processing the portable apparatus 120 data and communication devices for connecting the peripheral devices to the system 100.

The system 100 for providing collaborative patient information may comprise rehabilitation ecosystem (global and local), where the patient (user apparatus 120) is in the middle of healthcare process, software (core SW at server apparatus 130) that enables interactive communication between patient (user apparatus 120) and healthcare professionals (user apparatuses 160, 180), application software (browser SW in apparatuses 160, 180) tool for healthcare professionals to provide rehabilitation program to patient apparatuses 110, 120 and to monitor patient rehabilitation progress, application software (mobile SW in apparatuses 110, 120) for patient self-rehabilitation and on-line communication with healthcare professionals, a camera application for recording additional personalized exercises by the user apparatus 180 and an editing software tool for providing personal exercise descriptions.

In an embodiment, the system 100 may further comprise an external database 170. The external database 170 may comprise patient information, rehabilitation information, trauma information, history data, estimate information or such, maintained by another service provider that the service system provider of server 130. 131. The database 170 may be accessible to the network 150 over connection 171. The database 170 may have corresponding structure as the server apparatus 130, 131, for example. The external database 170 may comprise, for example, public healthcare service data server from where patient related data may be received. Furthermore, the external database 170 may also comprise, for example, third party service provider, such as an insurance company that may receive patient or rehabilitation related data from the server 130, 131.

Figure 2:
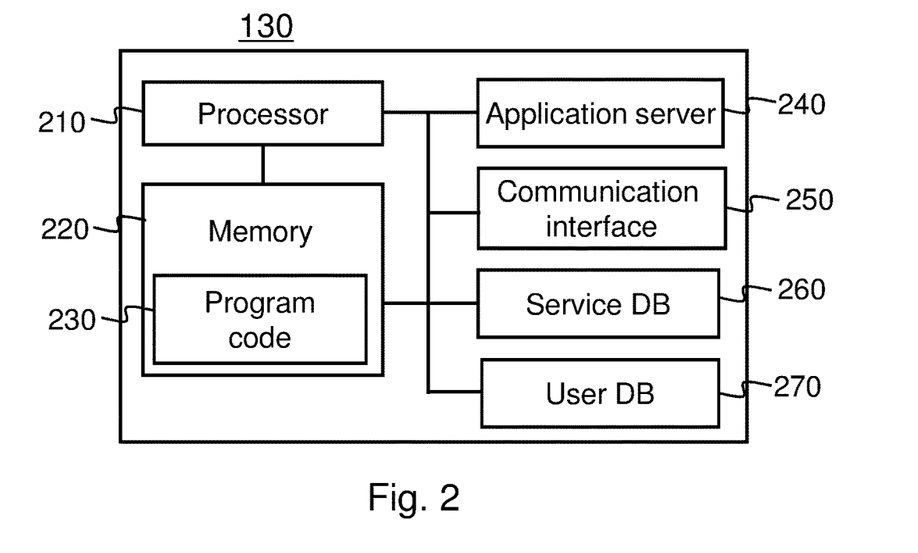
FIG. 2 shows a block diagram of the server apparatus of an example embodiment.

FIG. 2 presents an example block diagram of a server apparatus 130 in which various embodiments of the invention may be applied. All elements described in FIG. 2 are not necessary to be implemented in the same apparatus 130. The general structure of the server apparatus 130 comprises a processor 210, and a memory 220 coupled to the processor 210. The server apparatus 130 further comprises software 230 stored in the memory 220 and operable to be loaded into and executed in the processor 210. The software 230 may comprise one or more software modules and can be in the form of a computer program product.

The processor 210 may be, e.g., a central processing unit (CPU), a microprocessor, a digital signal processor (DSP), a graphics processing unit, or the like. FIG. 2 shows one processor 210, but the server apparatus 130 may comprise a plurality of processors.

The memory 220 may be for example a non-volatile or a volatile memory, such as a read-only memory (ROM), a programmable read-only memory (PROM), erasable programmable read-only memory (EPROM), a random-access memory (RAM), a flash memory, a data disk, an optical storage, a magnetic storage, a smart card, or the like. The server apparatus 130 may comprise a plurality of memories. The memory 220 may be constructed as a part of the server apparatus 130 or it may be inserted into a slot, port, or the like of the server apparatus 130 by a user. The memory 220 may serve the sole purpose of storing data, or it may be constructed as a part of an apparatus serving other purposes, such as processing data.

The communication interface module 250 implements at least part of data transmission. The communication interface module 250 may comprise, e.g., a wireless or a wired interface module. The wireless interface may comprise such as a WLAN, Bluetooth, infrared (IR), radio frequency identification (RF ID), GSM/GPRS, CDMA, WCDMA, or LTE (Long Term Evolution) radio module. The wired interface may comprise such as Ethernet or universal serial bus (USB), for example. The communication interface module 250 may be integrated into the server apparatus 130, or into an adapter, card or the like that may be inserted into a suitable slot or port of the server apparatus 130. The communication interface module 250 may support one radio interface technology or a plurality of technologies. Configuration information between the user apparatus 120 and the system server 130 may be transceived using the communication interface 250. Similarly, account creation information between the system server 130 and a service provider may be transceived using the communication interface 250.

An application server 240 provides application services e.g. relating to the user accounts stored in a user database 270 and to the service information stored in a service database 260. Different application services may be provided to different users, such as the first user (doctor), the second user (patient) and the third user (therapist). The service information may comprise patient trauma information, patient rehabilitation information, and patient feedback information, for example.

A skilled person appreciates that in addition to the elements shown in FIG. 2, the server apparatus 130 may comprise other elements, such as microphones, displays, as well as additional circuitry such as input/output (I/O) circuitry, memory chips, application-specific integrated circuits (ASIC), processing circuitry for specific purposes such as source coding/decoding circuitry, channel coding/decoding circuitry, ciphering/deciphering circuitry, and the like. In an embodiment, the server apparatus 130 may receive patient trauma information, maintain patient rehabilitation information based on the patient trauma information, associate the patient trauma information and the patient rehabilitation information with a patient identifier to provide a collaborative patient record, and automatically provide a set of exercises from a database based on the collaborative patient record. Furthermore, the server apparatus 130 may be configured to receive selection for at least one exercise from the set of exercises and providing audio-visual training information relating to the selected exercises to be added to the patient rehabilitation information, provide the audio-visual training information to be available for the patient, and receive feedback information relating to the training information and adding the feedback information to the collaborative patient record. An automatic alert may be determined using at least one of the following: the patient trauma information; the patient rehabilitation information; and the feedback information.

In an embodiment, feedback information given by a user, such as a patient, may relate to rehabilitation the patient is going through according to instructions given by a doctor and/or a therapist (physical or mental). The rehabilitation information maintained in the system may comprise rehabilitation diary for a plurality of (physical) exercises. It is important that the patient updates feedback relating to the rehabilitation progress to the system and that the responsible doctor and/or the therapist have access to the information as quickly as possible. The feedback information may relate, for example, to performed physical exercises according to the rehabilitation diary, medicines ordered by the doctor, state of swelling, sensation of pain in the rest, sensation of pain in the stress, estimate on general performance and patient's general daily comments.

Figure 3:
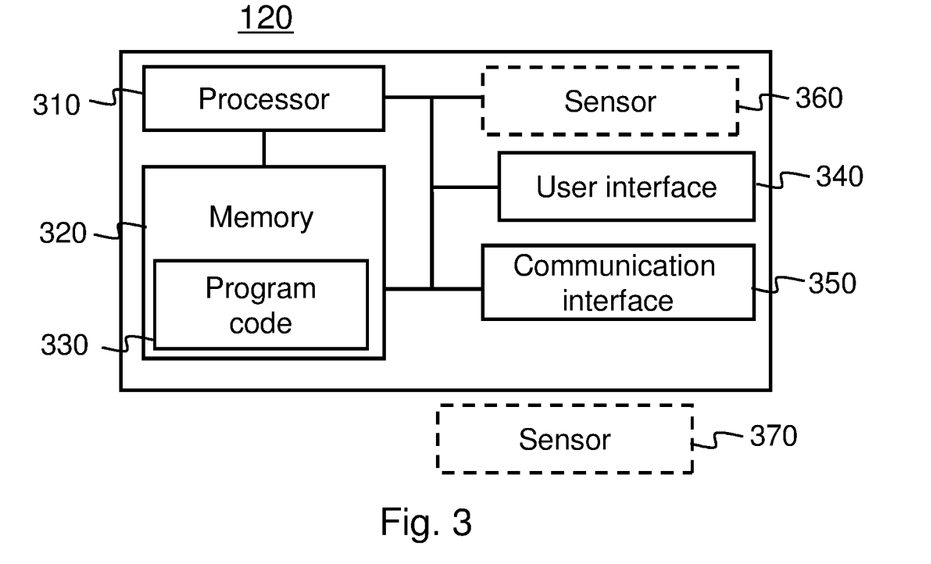
FIG. 3 shows a block diagram of a user apparatus of an example embodiment.

FIG. 3 shows a block diagram of a user apparatus of an example embodiment. In an embodiment, a sensor 360, 370 may be implemented as a separate device 370 communicating via the communication interface 350 with the apparatus 120, or as an integrated sensor 360 within the apparatus 120. The user interface 340 may be implemented also in another device connected via a communication interface 350 to the apparatus 120. Such device may comprise a mobile phone, a smart phone, or a tablet, for example. In an embodiment, the apparatus 120 may communicate with a plurality of sensors 360, 370, both internal and external sensors, and of a plurality of users. In an embodiment, the sensor 360 may also comprise a camera for capturing multimedia data to be submitted to the server apparatus 130, 131 for determination of preliminary trauma information or for creating multimedia data.

The general structure of the apparatus 120 comprises a user interface 340, a communication interface 350, a processor 310, and a memory 320 coupled to the processor 310. The apparatus 120 further comprises software 330 stored in the memory 320 and operable to be loaded into and executed in the processor 310. The software 330 may comprise one or more software modules and can be in the form of a computer program product. Not all elements of FIG. 3 are necessary but optional for the portable apparatus 120, such as the sensor 360, 370.

The processor 310 may be, e.g., a central processing unit (CPU), a microprocessor, a digital signal processor (DSP), a graphics processing unit, or the like. FIG. 3 shows one processor 310, but the apparatus 120 may comprise a plurality of processors.

The memory 320 may be for example a non-volatile or a volatile memory, such as a read-only memory (ROM), a programmable read-only memory (PROM), erasable programmable read-only memory (EPROM), a random-access memory (RAM), a flash memory, a data disk, an optical storage, a magnetic storage, a smart card, or the like. The apparatus 120 may comprise a plurality of memories. The memory 320 may be constructed as a part of the apparatus 120 or it may be inserted into a slot, port, or the like of the apparatus 120 by a user. The memory 320 may serve the sole purpose of storing data, or it may be constructed as a part of an apparatus serving other purposes, such as processing data.

The user interface 340 may comprise circuitry for receiving input from a user of the apparatus 120, e.g., via a keyboard, a touchpad, a motion sensor, a touch-screen of the apparatus 120, speech recognition circuitry, gesture recognition circuitry or an accessory device, such as a headset or a remote controller, for example. Furthermore, the user interface 340 may comprise circuitry for providing output for the user via a display, a speaker, a touch-sensitive display or a tactile feedback device, for example.

In an embodiment, a patient may speak during the (physical) exercise relating to sensations during the exercise and the speech is automatically converted to feedback information for the system. Thus feedback is always up-to-date and accurate.

The communication interface module 350 implements at least part of data transmission. The communication interface module 350 may comprise, e.g., a wireless or a wired interface module. The wireless interface may comprise such as a WLAN, Bluetooth, infrared (IR), radio frequency identification (RF ID), NFC, GSM/GPRS, CDMA, WCDMA, or LTE (Long Term Evolution) radio module. The wired interface may comprise such as universal serial bus (USB), HDMI, SCART or RCA, for example. The communication interface module 350 may be integrated into the apparatus 120, or into an adapter, card or the like that may be inserted into a suitable slot or port of the apparatus 120. The communication interface module 350 may support one radio interface technology or a plurality of technologies. The communication interface module 350 may support one wired interface technology or a plurality of technologies. The apparatus 120 may comprise a plurality of communication interface modules 350.

In an embodiment, the communication interface module 350 may comprise location modules for tracking location of the apparatus 120. Such location modules may comprise a module for satellite based global positioning system (e.g. GPS), a module for cellular based positioning system, a module for wireless non-cellular positioning system (e.g. Wi-Fi) or a module for hybrid positioning system, for example.

In an embodiment, the communication interface 350 with a satellite based global positioning system (e.g. GPS) may detect altitude of the user to provide an estimate of thinness of air. Such estimate of air thinness may be used as input for determining characteristics of the physical exercise for patient rehabilitation.

A skilled person appreciates that in addition to the elements shown in FIG. 3, the apparatus 120 may comprise other elements, such as microphones, speakers, sensors, cameras, as well as additional circuitry such as input/output (I/O) circuitry, memory chips, application-specific integrated circuits (ASIC), processing circuitry for specific purposes such as source coding/decoding circuitry, channel coding/decoding circuitry, ciphering/deciphering circuitry, and the like. Additionally, apparatus 120 may comprise a disposable or rechargeable battery (not shown) for powering when external power if external power supply is not available.

Figure 4:
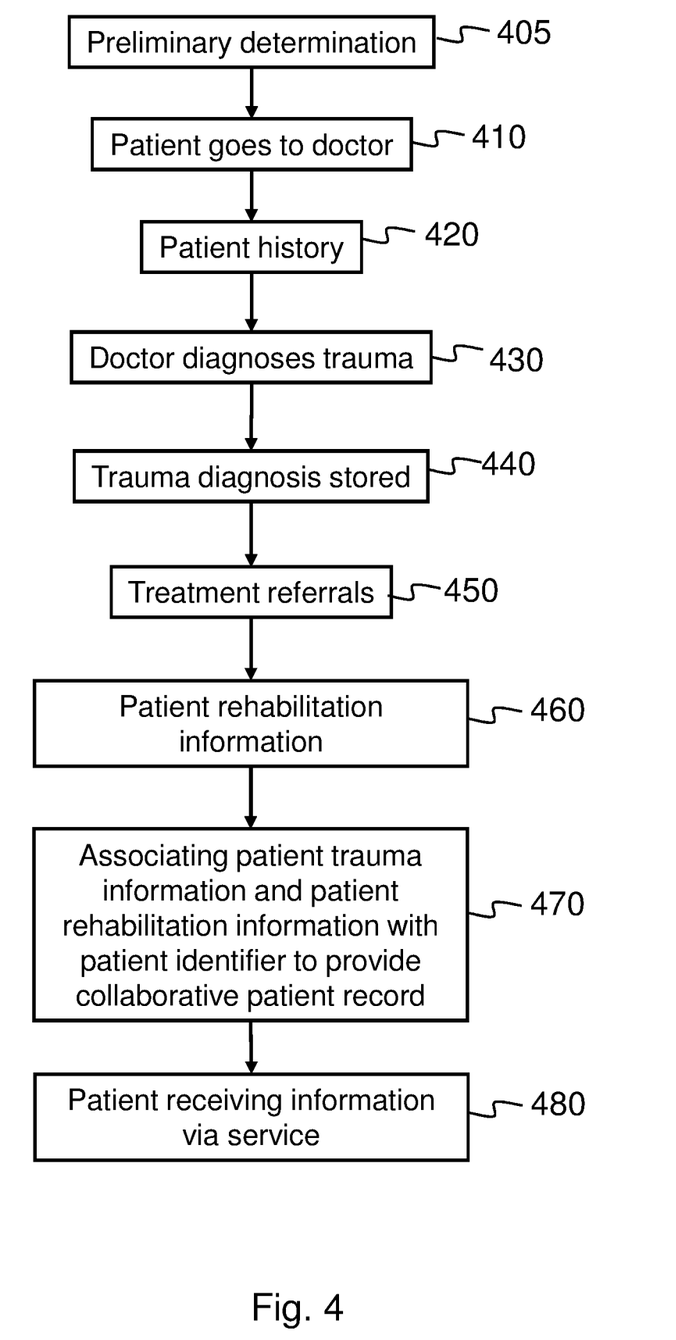
FIG. 4 shows a flow chart of a process of an example embodiment.

In an embodiment, the apparatus 120 comprises speech or gesture recognition means. Using these means, a pre-defined phrase or a gesture may be recognized from the speech or the gesture and translated into control information for the apparatus 120. FIG. 4 shows a flow chart of a process according to an example embodiment of the invention. Patient has after the very first visit to a doctor a comprehensive rehabilitation recommendation. Patient can download the recommendation to the mobile devices and computers as well as print it out. The process may even begin before the patient goes to see a doctor in step 410. Before that, in step 405, it may possible that preliminary trauma information is determined.

Preliminary determination 405 may comprise, for example, occupational health service periodical inspection, such as mammography, for example. Alternatively various physical movements of limbs or joints may be captured by multimedia data for preliminary trauma determination. The multimedia data may be sent to the system server 130, 131 for processing. The multimedia data may be compared to the history data of other patients and based on that a corresponding patient data record may be identified and further actions defined based on that. Further actions may comprise, for example, order to visit doctor as in step 410, order to visit a therapist as in step 510 of FIG. 5 or providing patient rehabilitation information as in step 460. When searching corresponding patient data records from the history data, sex, occupation, age and location may be used for filtering the data, for example.

Preliminary determination 405 may also comprise, for example, trauma rehabilitation, wherein a therapist may instruct the patient for capturing a multimedia data of the trauma. Capture may take place at the therapist by the therapist user apparatus with a camera or remotely by the patient by the patient user apparatus. The multimedia data may also be processed by the therapist user apparatus to provide further information of the trauma before sending the data to the server 130, 131, or the data may be send as such by the user apparatus of the therapist or the patient.

Preliminary determination 405 may also comprise, for example, evaluation of physical operability of a user. The user may be walking on a treadmill and using sensors (accelerometer, gyroscope etc.) and/or a camera application, multimedia data of the trauma may be identified and captured. The captured multimedia data may be sent to the server 130, 131 for automatic preliminary trauma determination.

Preliminary determination 405 may comprise, for example, objective health data captured by a sensor of a user apparatus 120 or a user device 110 operationally connected to the user apparatus 120 to operate as a sensor. Such health data may comprise, for example, blood pressure, heart rate, and blood sample related data.

In step 420, the service process may check from patient history data maintained in the service system, if the patient has visited a doctor earlier due to the same trauma. Doctor receives patient trauma history information, the earlier diagnoses, rehabilitations and their recommendations. The doctor may also study patient data, such as data saved by the patient, such as exercises, medicine, sensation of the pain, performance and comments. The doctor may use available information for the patient when evaluating patient trauma.

In step 430, the doctor diagnoses the patient trauma. If there are no patient history data available in the system, the step 420 may be skipped and process may move from step 410 directly to step 430. In step 440 of the process, the patient trauma diagnosis is stored to the service system as patient trauma information.

In step 450, the doctor may define or update patient's physiotherapeutic examination and treatment referrals that are automatically stored into the service system server. The service system may automatically receive patient trauma information and patient history data as input, and provide a default set of physiotherapeutic treatments based on the input. The doctor may use this default set when defining further actions. The stored data is immediately visible to all relevant parties, such as the patient and the physiotherapist, for example.

In step 460, the doctor defines patient rehabilitation targets and recommendations, and assesses the level of the trauma. Again, patient history data and earlier rehabilitation information may be used by the system as input when providing the doctor a default set of rehabilitation options to start with. Furthermore, based on the patient information available in the system, other patients' data mapping to similar patient profile (sex, age, trauma history etc.) may be used to provide default rehabilitation information for the trauma. The doctor may further add nutrition guides and accept the predefined rehabilitation recommendation for the diagnosed trauma. Thus, overall patient rehabilitation information is generated based on the patient trauma information and maintained in the system server. The patient trauma information and the patient rehabilitation information are associated with a patient identifier to provide a collaborative patient record in step 470.

In step 480, the patient may access the collaborative patient record and receive rehabilitation recommendation to be followed via a client application of patient user apparatus, for example.

Figure 5:
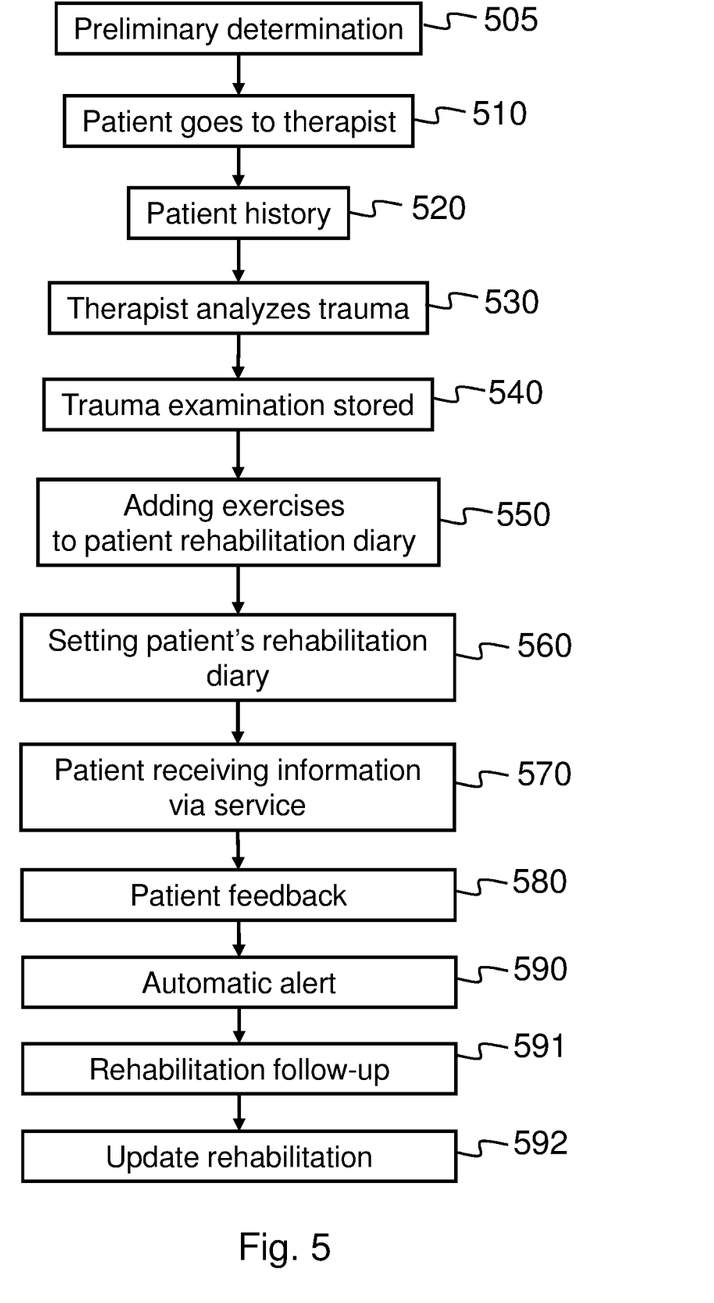
FIG. 5 shows a flow chart of a process according to another example embodiment.

FIG. 5 shows a flow chart of a process according to another example embodiment of the invention. A therapist (e.g. a physiotherapist) may utilize the service system together with the doctor and the patient. The process begins when a patient goes to see a therapist in step 510. This step 510 may take after process steps disclosed in FIG. 4 or before those steps. However, even before step 510, in step 505, it may possible that preliminary trauma information is determined.

Preliminary determination 505 may comprise, for example, occupational health service periodical inspection, such as mammography, for example. Alternatively various physical movements of limbs or joints may be captured by multimedia data for preliminary trauma determination. The multimedia data may be sent to the system server 130, 131 for processing. The multimedia data may be compared to the history data of other patients and based on that a corresponding patient data record may be identified and further actions defined based on that. Further actions may comprise, for example, order to visit doctor as in step 410 of FIG. 4, order to visit a therapist as in step 510 of FIG. 5 or setting patient rehabilitation diary as in step 560. When searching corresponding patient data records from the history data, sex, occupation, age and location may be used for filtering the data, for example.

Preliminary determination 505 may also comprise, for example, trauma rehabilitation, wherein a therapist may instruct the patient for capturing a multimedia data of the trauma. Capture may take place at the therapist by the therapist user apparatus with a camera or remotely by the patient by the patient user apparatus. The multimedia data may also be processed by the therapist user apparatus to provide further information of the trauma before sending the data to the server 130, 131, or the data may be send as such by the user apparatus of the therapist or the patient.

Preliminary determination 505 may also comprise, for example, evaluation of physical operability of a user. The user may be walking on a treadmill and using sensors (accelerometer, gyroscope etc.) and/or a camera application, multimedia data of the trauma may be identified and captured. The captured multimedia data may be sent to the server 130, 131 for automatic preliminary trauma determination.

Preliminary determination 505 may comprise, for example, objective health data captured by a sensor of a user apparatus 120 or a user device 110 operationally connected to the user apparatus 120 to operate as a sensor. Such health data may comprise, for example, joint movement data, blood pressure, heart rate, and blood sample related data.

In step 520, the service process may check from patient history data maintained in the service system, if the patient has visited a doctor or therapist earlier due to the same trauma. The therapist receives patient trauma history information, the earlier diagnoses, rehabilitations and their recommendations. The therapist may also study patient data, such as data saved by the patient, exercises, medicine, sensation of the pain, performance and comments. The therapist may use available information for the patient when evaluating patient trauma and rehabilitation needs.

In step 530, the therapist (e.g. physiotherapist) analyses the patient trauma. If there are no patient history data available in the system, the step 520 may be skipped and process may move from step 510 directly to step 530. In step 540 of the process, the patient trauma examination may be stored to the service system as patient trauma information.

In an embodiment, patient trauma information may be received and patient rehabilitation information is generated based on the patient trauma information. Furthermore, the patient trauma information and the patient rehabilitation information are associated with a patient identifier to provide a collaborative patient record.

In step 550, the therapist may add exercises (e.g. physical or mental) to the patient's rehabilitation diary maintained in the service system. In an embodiment, the system may automatically provide a set of exercises from a database based on the collaborative patient record for the therapist to start on.

In step 550, the therapist (e.g. physiotherapist) may select at least one exercise from the set of exercises (e.g. physical or mental) and provide audio-visual training information relating to the selected exercises to be added to the patient rehabilitation information.

The exercises may be selected in step 550 in different ways. First, the exercise with audio-visual training information may be selected from a library maintained at the server apparatus 130. Second, the exercise with audio-visual training information may be selected from a library maintained at the user apparatus 180 of the physiotherapist. Third, the physiotherapist may activate a camera application operationally connected to the service system, record a new exercise and add necessary audio-visual information, such as video, images and speech, for example. The new exercise may then be added to the libraries for exercises (e.g. physical or mental) maintained in the server 130 or the user apparatus 180 for later selection.

After selection of at least one exercise, the selected exercise(s) is/are added to the patient's rehabilitation diary. In step 560, further details for the patient's rehabilitation diary may be set, such as daily exercise sessions for each exercise defining the series and repetitions, for example. After that the patient's rehabilitation diary for the exercises and associated audio-visual training information is made available for the patient using the system service, as illustrated in step 570. The patient can continue to use updated patient rehabilitation diary for the entire rehabilitation period.

In step 580 of the process, the patient transmits feedback information to the system server relating to the training information and the feedback information is added to the collaborative patient record in the server 130. The feedback information may also comprise any feedback relating to the rehabilitation or patients health status. The feedback may comprise, for example patient's opinion on pain, swelling, sensation/feeling, subjective status and objective status. The subjective status may comprise patient's own estimate of his/her physical or mental health. The objective status may comprise health related data from various sensors, user devices (such as blood pressure measuring device) or laboratory results, for example.

In step 590, an automatic alert is determined by the process run in the system using at least one of the following: the patient trauma information, the patient rehabilitation information, and the feedback information.

In an embodiment, the automatic alert is based on the dynamic rehabilitation diary and the automatic alert is sent to a user apparatus of the patient. The automatic alert may also be sent to a user apparatus of a doctor providing the patient trauma information and/or to a user apparatus of a physiotherapist providing the selection for at least one physical exercise of the patient rehabilitation information.

In an embodiment, rehabilitation may be followed up in step 591. Further feedback for questionnaires may be activated for estimating the status of rehabilitation. Feedback information may be requested in step 580 after each exercise (e.g. physical or mental) being performed based on changed performance status of the exercise in the dynamic rehabilitation diary. Furthermore, the requested feedback comprises a pain scale questionnaire to be answered by the patient in step 580 and/or step 591.

In an embodiment, after receiving answers to the pain scale questionnaire in step 591, the answers are converted to the feedback information relating to the training information and the system further adds the feedback information to the collaborative patient record, and the service system may generate a report based on the feedback information.

The feedback information may comprise patient's opinion on pain, swelling, sensation/feeling, subjective status and objective status. The subjective status may comprise patient's own estimate of his/her physical or mental health. The objective status may comprise health related data from various sensors, user devices (such as blood pressure measuring device) or laboratory results, for example.

The report may be sent to a user apparatus of a doctor providing the patient trauma information and/or to a user apparatus of a physiotherapist providing the selection for at least one exercise of the patient rehabilitation information.

In an embodiment, the automatic alert of 590 to a user apparatus of the patient comprises instructions to perform an exercise (e.g. physical or mental) defined by the dynamic rehabilitation diary.

In an embodiment, the physiotherapist may follow the progress of the patient rehabilitation in step 592 based on the diary and the feedback information, and define an update for the dynamic rehabilitation diary defining the at least one exercise; and update the dynamic rehabilitation diary defining the at least one exercise to be performed in a timely manner.

In an embodiment, the dynamic rehabilitation diary may define a plurality of exercises each to be performed in a timely manner.

Figure 6:
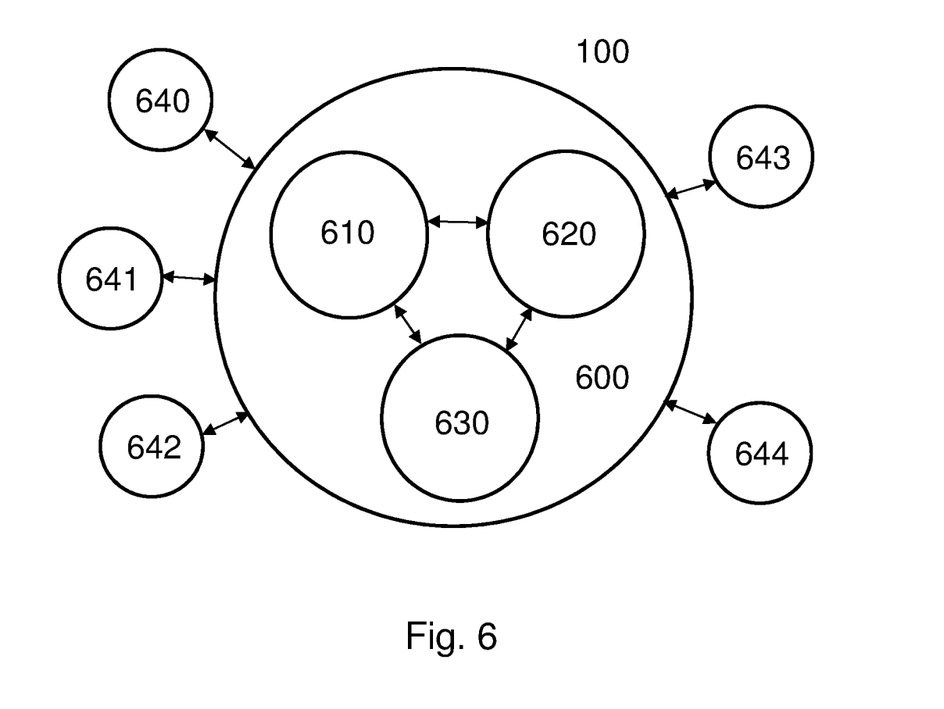
FIG. 6 shows a schematic illustration of different users of the service system according to an embodiment.

FIG. 6 shows a schematic illustration of different users of the service system 100 according to an embodiment. The service system 100 comprises three main users. A first user 610, a second user 620 and a third user 630. The first user 610 may comprise a doctor, the second user 620 may comprise a patient, and the third user 630 may comprise a therapist (physical or mental), for example. All three users 610-630 may generate collaborative patient information 600 to be maintained in the service system 100. The collaborative patient information 600 may be maintained as a collaborative patient record within the server 130, 131.

In an embodiment, external users 640-644 may be connected to the service system 100 to have access to at least a pre-defined portion of the collaborative patient information 600. The access for the users 640-644 may be limited to certain patient(s) 620 and/or certain parts of the collaborative patient information 600.

External users may comprise, but are not limited to, a relative 640 of the patient 620, an insurance company 641 of the patient 620, public health care 642 of the patient 620, an employer 643 of the patient 620 or a health care clinic 644 of the patient 620, for example. The relative 640 or a person from health care clinic 644 may comprise a care person 640, 644 that is a dedicated person having access to at least part of the collaborative patient record and looking after the patient trauma and rehabilitation.

In an embodiment the relative 640 may have access from a remote user apparatus, corresponding to at least one of the user apparatuses 120, 160, 180 illustrated in FIG. 1, and have access to the collaborative patient information maintained in the system server 130 of the service system 100. The relative user 640 may access information 600 relating to the persons 610, 630 who are part of the patient's 620 treatment. Thus, the relative 640 can contact right persons if needed. The relative user 640 may also access information 600 about the patient trauma to decrease uncertainty and eliminate misunderstanding. The relative user 640 may also access information 600 on how the patient 620 can be rehabilitated back to normal performance. Such information improves relatives' atmosphere and helps to encourage the patient. Access to the information 600 also enables the relative user 640 to follow the patient's rehabilitation progress and reporting. Such following helps the relative user 640 to realize the progress and patient's 620 motivation for the rehabilitation. If the patient 620 can't report of giver feedback information to the system 100, the rehabilitation progress relative 640 can do it for him/her. The relative user 640 may also access information 600 for following the sensation of the pain and recommended diet to better understand and support the patient 620 progress.

In an embodiment the employer user 643 may have access from a remote user apparatus, corresponding to at least one of the user apparatuses 120, 160, 180 illustrated in FIG. 1, and have access to the collaborative patient information maintained in the system server 130 of the service system 100. The employer user 643 may access information 600 about the patient's (employee) trauma to decrease uncertainty and eliminate misunderstanding. The employer user 643 may also have access for information on how the patient can be rehabilitated back to normal performance to make it easier to forecast when employee comes back to work. Furthermore, by following the patient rehabilitation progress and reporting using the system 100, it helps the employer to plan on deputes for the patient. The collaborative patient information 600 may also provide Information of average rehabilitation period duration for the trauma of the patient to help the employer to control health care costs and quality development.

In an embodiment the health care user 642,644 may have access from a remote user apparatus, corresponding to at least one of the user apparatuses 120, 160, 180 illustrated in FIG. 1, and have access to the collaborative patient information maintained in the system server 130 of the service system 100. The health care user 642,644 may access information 600 relating to entire ecosystem (patients of the healthcare, for example) for rehabilitation. Such information produces reliable and real time data for health care operations and helps to define quality improvement. The health care user 642,644 may also have access to real information rehabilitation period and it's progress directly for a certain patient. Such information helps to control health care costs and quality development. Following the patient's rehabilitation progress and reporting provides information of treatment effectiveness, analysis, measuring and reporting. Then again, having access to information 600 relating to sensation of the pain and to the recommended diet provides information of treatment effectiveness for further analysis and creates possibilities for new business. Alerts may be used as well for health care users 642,644 to indicate the users 642,644 if the rehabilitation does not progress according to the plan.

In an embodiment the insurance company user 641 may have access from a remote user apparatus, corresponding to at least one of the user apparatuses 120, 160, 180 illustrated in FIG. 1, and have access to the collaborative patient information maintained in the system server 130 of the service system 100. The insurance company user 641 may access information 600 relating to real time information for the rehabilitation recommendations, periods and progress for different traumas. That provides a possibility to develop new products. The insurance company user 641 may further access information 600 on how patients 620 are rehabilitated. Such access provides reliable information directly for certain patients and improves follow up of rehabilitation effectiveness. The insurance company user 641 may also access information of needed doctor and physiotherapist visits for different traumas to improve estimation of cost claims. The insurance company user 641 may further measure health care users 642,644, rehabilitation partners 630 and other parties involved in the rehabilitation process to improve future partner selections and to increase e-services and their quality, for example. The service system 100 offers a digital environment where healthcare professionals 610, 630 can interactively communicate with patients 620 and support their needs on-line.

Without in any way limiting the scope, interpretation, or application of the claims appearing below, a technical effect of one or more of the example embodiments disclosed herein is improved method and apparatus for providing collaborative patient information. Another technical effect of one or more of the example embodiments disclosed herein is improved accuracy of the patient information relating to a trauma. Another technical effect of one or more of the example embodiments disclosed herein is that a plurality of users linked with the patient's trauma rehabilitation may have up-to-date access to all patient information relevant for the rehabilitation process. Another technical effect of one or more of the example embodiments disclosed herein is that external users required to have information of the progress of the rehabilitation process and its progress may have access to the latest information in a dynamic way by giving permissions to such external users to certain parts of the collaborative patient information. Another technical effect of one or more of the example embodiments disclosed herein is that only a single system is need for all and no complex apparatuses are needed, and a wide variety of mobile devices, smartphones, tablets and computers may be used to provide more simple system.

In an embodiment, each user may be identified by a user identifier, such as a social security number or personal e-mail address that may be verified when a user profile is created to the system. Each user may define access rights to other users within the system for certain parts of the information within the collaborative patient record.

If desired, the different functions discussed herein may be performed in a different order and/or concurrently with each other. Furthermore, if desired, one or more of the before-described functions may be optional or may be combined.

Although various aspects of the invention are set out in the independent claims, other aspects of the invention comprise other combinations of features from the described embodiments and/or the dependent claims with the features of the independent claims, and not solely the combinations explicitly set out in the claims.

However, claimed embodiments do not constitute a method step for treatment of the human or animal body by surgery or therapy. No functional relationship exists between the steps related to apparatus and any therapeutic effect of the apparatus on the body.

The invention claimed is:

1. A server apparatus comprising:
   a communication interface for transceiving information over a network;
   at least one memory including computer program code;
   the at least one memory and the computer program code configured to, with the at least one processor, cause the apparatus to:
   receive second user multimedia trauma data captured by the second user, from a user apparatus of the second user;
   maintain history data of a plurality of reference collaborative patient records of other patients comprising information on multimedia data for different patient traumas;
   automatically compare the received second user multimedia trauma data with the history data;
   automatically select, based on the comparison, at least one reference collaborative patient record of another patient, wherein the comparison or the selection step comprises automatic analysis with pattern recognition or image recognition;
   automatically determine, based on the selected reference collaborative patient record of another patient, second user patient trauma information;
   generate patient rehabilitation information based on the second user patient trauma information;
   associate the second user patient trauma information and the patient rehabilitation information with a patient identifier to provide a second user collaborative patient record accessible by a first user, the second user and a third user, wherein the first user comprises a doctor, the second user comprises a patient, and the third user comprises a therapist;
   use the server apparatus to automatically provide a set of physical exercises from a database based on the second user collaborative patient record;
   receive selection, by the third user, of at least one physical exercise from the set of physical exercises and providing audio-visual training information relating to the selected physical exercises to be added to the patient rehabilitation information; and
   provide the audio-visual training information to be available for the patient.

2. The server apparatus of claim 1, wherein the at least one memory and the computer program code further configured to, with the at least one processor, cause the apparatus to:
   maintain history data of a plurality of reference collaborative patient records of other patients comprising information on rehabilitation times for different patient traumas;
   compare the received patient trauma information with the history data;
   select, based on the comparison, at least one reference collaborative patient record; and
   determine an estimated rehabilitation time for the patient based on the selected reference collaborative patient record and the collaborative patient record.

3. The server apparatus of claim 2, wherein the at least one memory and the computer program code further configured to, with the at least one processor, cause the apparatus to:
   determine, based on the selected reference collaborative patient record and the collaborative patient record, selection for at least one further physical exercise from the set of physical exercises and providing audio-visual training information relating to the selected physical exercises to be added to the patient rehabilitation information; and
   provide the audio-visual training information to be available for the patient.

4. The server apparatus of claim 1, wherein
   the first, second and third user are configured to generate collaborative patient information maintained as a collaborative patient record within the server apparatus.

5. The server apparatus of claim 1, wherein the at least one memory and the computer program code further configured to, with the at least one processor, cause the apparatus to:
   determine, based on the selected reference collaborative patient record, preliminary patient trauma information;
   provide the preliminary patient trauma information for an approval to a first user; and
   receive patient trauma information in response to the approval from the first user.

6. The server apparatus of claim 1, wherein the at least one memory and the computer program code further configured to, with the at least one processor, cause the apparatus to:
   receive feedback information relating to the training information and adding the feedback information to the collaborative patient record; and
   determine an automatic alert using at least one of the following:
   the patient trauma information;
   the patient rehabilitation information; and
   the feedback information.

7. The server apparatus of claim 6, wherein the exercise comprising at least one of a physical exercise and a mental exercise, and the patient rehabilitation information comprising a dynamic rehabilitation diary defining the exercise to be performed in a timely manner and maintaining status of the performance of the exercise, and wherein the at least one memory and the computer program code further configured to, with the at least one processor, cause the apparatus to:
determine the automatic alert based on the dynamic rehabilitation diary;
send the automatic alert to a user apparatus of the patient; and
send the automatic alert to at least one of the following: a user apparatus of a doctor providing the patient trauma information; and a user apparatus of a physiotherapist, wherein the automatic alert to the user apparatus of the patient comprising instructions to perform a physical exercise defined by the dynamic rehabilitation diary and providing the selection for at least one physical exercise of the patient rehabilitation information.

8. The server apparatus of claim 7, wherein the at least one memory and the computer program code further configured to, with the at least one processor, cause the apparatus to receive an update for the dynamic rehabilitation diary defining the at least one physical exercise; and update the dynamic rehabilitation diary defining the at least one physical exercise to be performed in a timely manner.

9. The server apparatus of claim 7, wherein the at least one memory and the computer program code further configured to, with the at least one processor, cause the apparatus to request feedback information after each physical exercise being performed based on changed performance status of the physical exercise in the dynamic rehabilitation diary, wherein the requested feedback comprising a pain scale questionnaire.

10. The server apparatus of claim 9, wherein the at least one memory and the computer program code further configured to, with the at least one processor, cause the apparatus to receive answers to the pain scale questionnaire, convert the answers to the feedback information relating to the training information, and add the feedback information to the collaborative patient record; generate a report based on the feedback information; and send the report to at least one of the following: a user apparatus of a care person; a user apparatus of a doctor providing the patient trauma information; and a user apparatus of a physiotherapist providing the selection for at least one physical exercise of the patient rehabilitation information.

11. A user apparatus comprising:
a sensor used by a second user to capture the second user's multimedia health data;
a communication interface for transceiving information over a network;
at least one memory including computer program code; the at least one memory and the computer program code configured to, with the at least one processor, cause the apparatus to:
transmit the second user's multimedia data for a server apparatus for patient trauma information determination, wherein at the server apparatus, history data is maintained of a plurality of reference collaborative patient records of other patients comprising information on multimedia data for different patient traumas; the received second user's multimedia health data is automatically compared with the history data; based on the comparison, at least one reference collaborative patient record of another patient is automatically selected, wherein the comparison or the selection step comprises patient trauma information is automatically determined based on the selected reference collaborative patient record of another patient; patient rehabilitation information is generated based on the second user's patient trauma information; the second user's patient trauma information and the patient rehabilitation information are associated with a patient identifier to provide a second user collaborative patient record accessible by a first user, the second user and a third user of the user apparatus, wherein the first user comprises a doctor, the second user comprises a patient, and the third user comprises a therapist; using the apparatus for automatically generating a set of exercises from a database based on the second user collaborative patient record; receiving a selection of at least one exercise from the set of exercises and providing audio-visual training information relating to the selected exercises to be added to the patient rehabilitation information; and the audio-visual training information being available for the user of the user apparatus.

12. The user apparatus of claim 11, comprising a client application of a collaboration patient data service whose server application is running on the server apparatus, wherein the client application is configured to capture the multimedia data.

13. The user apparatus of claim 12, wherein the multimedia data comprising a still image or a video stream.

14. The user apparatus of claim 12, wherein the client application is configured to retrieve metadata for the captured multimedia data from metadata elements of the user apparatus.

15. The user apparatus of claim 12, wherein the client application of the user apparatus is configured to access the collaborative patient record and receive rehabilitation recommendation to be followed by the user of the user apparatus.

16. A computer program comprising computer executable program code configured to control an apparatus, when the computer executable program code is executed, to:
receive second user multimedia trauma data captured by the second user, from a user apparatus of the second user;
maintain history data of a plurality of reference collaborative patient records of other patients comprising information on multimedia data for different patient traumas;
automatically compare the received multimedia data with the history data;
automatically select, based on the comparison, at least one reference collaborative patient record of another patient, wherein the comparison or the selection step comprises automatic analysis with pattern recognition or image recognition;
automatically determine, based on the selected reference collaborative patient record of another patient, second user patient trauma information;
generate patient rehabilitation information based on the second user patient trauma information;
associate the second user patient trauma information and the patient rehabilitation information with a patient identifier to provide a second user collaborative patient record accessible by a first user, the second user and a third user, wherein the first user comprises a doctor, the second user comprises a patient, and the third user comprises a therapist;

use the apparatus to automatically provide a set of physical exercises from a database based on the second user collaborative patient record; and receive selection, from the third user, for at least one physical exercise from the set of physical exercises and provide audio-visual training information relating to the selected physical exercises to be added to the patient rehabilitation information.

17. A method, at a service server apparatus, for providing collaborative patient information, the method comprising:

receiving second user multimedia trauma data captured by the second user, from a user apparatus of the second user;

maintaining history data of a plurality of reference collaborative patient records of other patients comprising information on multimedia data for different patient traumas;

automatically comparing the received multimedia data with the history data;

automatically selecting, based on the comparison, at least one reference collaborative patient record of another patient, wherein the comparison or the selection step comprises automatic analysis with pattern recognition or image recognition;

automatically determining, based on the selected reference collaborative patient record of another patient, second user patient trauma information;

generating patient rehabilitation information based on the patient trauma information;

associating the second user patient trauma information and the patient rehabilitation information with a patient identifier to provide a second user collaborative patient record accessible by a first user, the second user and a third user, wherein the first user comprises a doctor, the second user comprises a patient, and the third user comprises a therapist;

using a server apparatus for automatically providing a set of exercises from a database based on the collaborative patient record;

receiving selection for at least one exercise from the set of exercises and providing audio-visual training information relating to the selected exercises to be added to the patient rehabilitation information; and providing the audio-visual training information to be available for the patient.

18. The method of claim 17, further comprising:

automatically analysing the received multimedia data at the system server to generate preliminary patient trauma information, wherein the automatic analysing comprises one or more of pattern recognition or image recognition.

19. The method of claim 17, further comprising:

capturing objective health data by a sensor of a user apparatus or a user device operationally connected to the user apparatus to operate as a sensor, wherein the objective health data is used for determining patient trauma information.

20. The method of claim 19, wherein the objective health data comprising at least one of the following: joint movement data, blood pressure, heart rate, and blood sample related data.

* * * * *